(12) United States Patent
Jones et al.

(10) Patent No.: US 7,142,625 B2
(45) Date of Patent: Nov. 28, 2006

(54) NUCLEAR MATERIAL DETECTION APPARATUS AND METHOD

(76) Inventors: James L. Jones, 1181 Kortnee Dr., Idaho Falls, ID (US) 83402; Jerry M. Hoggan, 2450 Ross Ave., Idaho Falls, ID (US) 83406; Yale D. Harker, 1903 W. 49 South, Idaho Falls, ID (US) 83402; Woo Y. Yoon, 5855 Leonard Ave., Idaho Falls, ID (US) 83401; Larry O. Johnson, 3581 2nd St., Island Park, ID (US) 83429

( * ) Notice: Subject to any disclaimer, the term of this patent is extended or adjusted under 35 U.S.C. 154(b) by 55 days.

(21) Appl. No.: 10/703,863

(22) Filed: Nov. 7, 2003

(65) Prior Publication Data
US 2005/0135534 A1    Jun. 23, 2005

(51) Int. Cl.
*G01T 3/00*    (2006.01)
(52) U.S. Cl. ............................ 376/153; 250/390.01
(58) Field of Classification Search ............. 376/153; 250/390.01
See application file for complete search history.

(56) References Cited

U.S. PATENT DOCUMENTS

| | | | | |
|---|---|---|---|---|
| 3,030,511 A | * | 4/1962 | Scherbatskoy | 250/264 |
| 3,296,440 A | * | 1/1967 | Schultz et al. | 376/254 |
| 3,358,142 A | * | 12/1967 | Hopkinson et al. | 250/262 |
| 3,439,165 A | * | 4/1969 | Hopkinson et al. | 250/262 |
| 3,569,701 A | * | 3/1971 | Satterfield et al. | 250/207 |
| 3,621,255 A | * | 11/1971 | Schwartz | 250/265 |
| 3,667,065 A | * | 5/1972 | Beurrier et al. | 330/124 R |
| 3,982,131 A | * | 9/1976 | Haller | 250/390.01 |
| 4,497,768 A | * | 2/1985 | Caldwell et al. | 376/153 |
| 4,655,994 A | * | 4/1987 | Greenberg | 376/254 |
| 5,098,640 A | * | 3/1992 | Gozani et al. | 376/166 |
| 5,237,493 A | * | 8/1993 | Durig et al. | 363/73 |
| 5,828,069 A | * | 10/1998 | Umiastowski et al. | 250/390.01 |
| 5,838,759 A | | 11/1998 | Armistead | |

* cited by examiner

*Primary Examiner*—Ricardo J. Palabrica
(74) *Attorney, Agent, or Firm*—Klaas, Law, O'Meara (57) ABSTRACT

A device for detecting photonuclear-induced neutrons is described herein. One embodiment of the device may comprise a neutron detector and a detection circuit. The neutron detector may comprise a detector output. The detection circuit may be operatively connected to the detector output and may comprise an amplifier, a low-pass filter, and a high pass filter. The amplifier may comprise an amplifier input and an amplifier output. The amplifier input may be being operatively connected to the detector output. The low-pass filter may comprise a low-pass filter input and a low-pass filter output. The low-pass filter input may be operatively connected to the amplifier output. The high-pass filter may comprise a high-pass filter input and a high-pass filter output. The high-pass filter input may be operatively connected to the amplifier output.

18 Claims, 7 Drawing Sheets

NUCLEAR MATERIAL DETECTION APPARATUS AND METHOD

CONTRACTUAL ORIGIN OF THE INVENTION

This invention was made with United States Government support under Contract No. DE-AC07-94ID13223, now Contract No. DE-AC07-99ID13727 awarded by the United States Department of Energy. The United States Government has certain rights in the invention.

TECHNICAL FIELD OF THE INVENTION

The present invention relates to the detection of nuclear materials, such as highly enriched uranium (HEU).

BACKGROUND OF THE INVENTION

With ever increasing demands for international trade and commerce, it is becoming more difficult to monitor the importation or smuggling of dangerous materials into a country. One very dangerous item that may be illegally imported into a country is nuclear material, such as highly enriched uranium (HEU). While any undeclared nuclear material is of concern and needs to be detected, HEU is of particular concern. HEU is a primary nuclear weapons component and can be used in limited quantities to produce an effective weapon of mass destruction. HEU is very difficult to detect in any shielded configuration due to its very low radioactive decay emissions. For example, HEU has a half life of $3.5 \times 10^{17}$ years with a neutron emission of $2 \times 10^{-4}$ n/s/g and a 186-keV gamma-ray emission that is easily shielded. Therefore, countries have to monitor their borders for nuclear materials in order to prevent adverse parties from building and detonating nuclear-type weapons within their borders.

The problem of detecting the importation of nuclear materials is exacerbated by the high quantity of international trade in the world. For example, a port-of-entry typically has too many containers entering the country to individually inspect each container for nuclear materials and other contraband. The major problem with any manual container inspection is that the inspection process is extremely tedious and costly due to the large container sizes and voluminous quantities of goods involved.

Nondestructive detection techniques of nuclear materials are characterized as passive or active depending on whether they measure radiation from the spontaneous decay of the nuclear material or from the radiation induced by an external interrogating source. Passive techniques can provide some capability in detecting nuclear materials; however, these techniques are limited due to the wide variety of possible nuclear material shielding configurations and the physical positioning within these large cargo containers. As indicated previously, the detection of HEU is even more difficult for passive detection techniques due to its very low radiation emissions.

Low radiation emission levels from nuclear materials, whether emitted directly or as a result of attenuation from neutron/gamma shielding, require very sensitive detectors to enable detection. Even with the most sensitive detectors, the detection of nuclear material is limited by the detectors' ability to distinguish natural background signals from the radiation generated by the nuclear material. Hence, in most cases involving containerized cargo, the passive detection techniques are challenged in the detection of most shielded nuclear materials, and especially shielded HEU.

One active interrogation technique, using an external neutron source (isotope or neutron generator), can be used to detect nuclear materials via the neutron multiplication effect from the fissioning-events in nuclear materials. Unfortunately, discriminating between the external neutrons emitted by the interrogating source and the induced neutrons from the nuclear material is difficult within a large-volume environment, such as a cargo container. In addition, this technique is application limited because of the administrative restrictions on the required neutron source strength involved and the associated neutron energy, slowing-down considerations.

Therefore, a need exists to overcome the above-described problems.

SUMMARY OF THE INVENTION

A device for detecting photonuclear-induced neutrons is described herein. One embodiment of the device may comprise a neutron detector and a detection circuit. The neutron detector may comprise a detector output. The detection circuit may be operatively connected to the detector output and may comprise an amplifier, a low-pass filter, and a high pass filter. The amplifier may comprise an amplifier input and an amplifier output. The amplifier input may be being operatively connected to the detector output. The low-pass filter may comprise a low-pass filter input and a low-pass filter output. The low-pass filter input may be operatively connected to the amplifier output. The high-pass filter may comprise a high-pass filter input and a high-pass filter output. The high-pass filter input may be operatively connected to the amplifier output.

DETAILED DESCRIPTION

Figure 1:
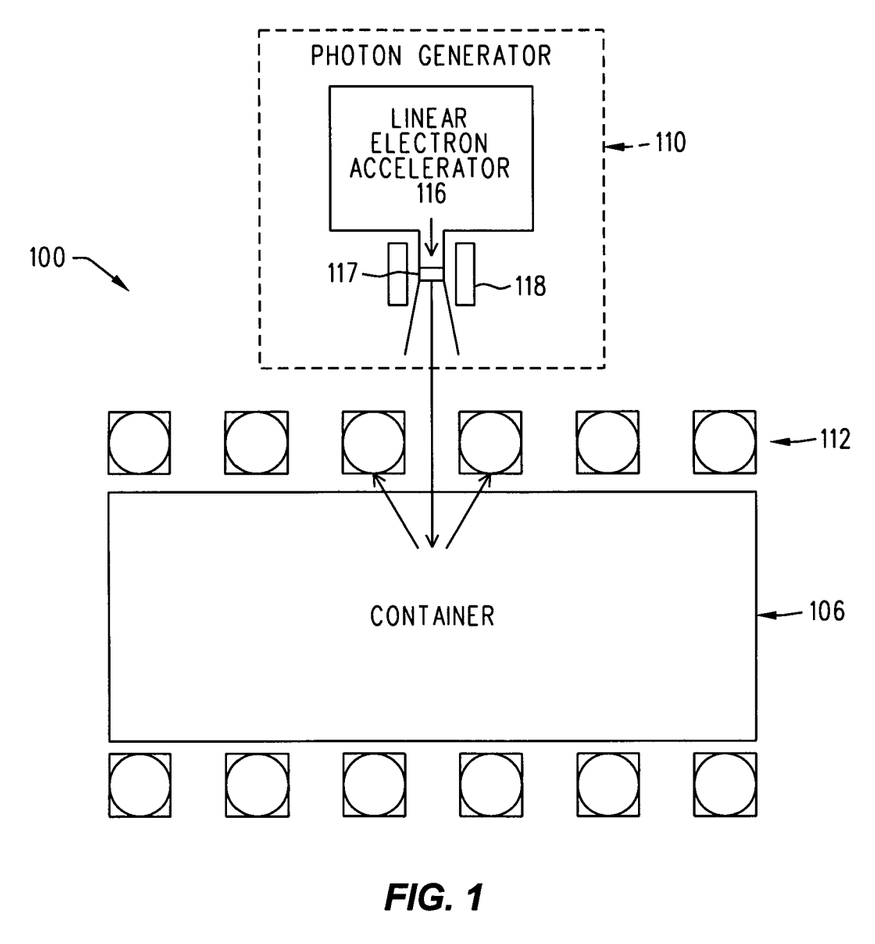
FIG. 1 is a top plan view of an embodiment of a nuclear detection system determining whether a container contains nuclear material.

A non-limiting embodiment of a interrogation system 100 used to detect the presence of nuclear materials, such as highly enriched uranium (HEU), is shown in FIG. 1. In the non-limiting example described herein, a container 106 is, or contains, the material to which a determination is being made regarding its nuclear material contents. It is to be noted that the example of the interrogation system 100 provided herein determines whether HEU, or any nuclear material, is present in the container 106. The container 106 is illustrated as being a shipping container such as those used by cargo container ships. It is to be understood, however, that the container 106 may be virtually any container capable of transporting or smuggling nuclear materials. For example, the container 106 may be a truck or as small as a 55-gallon drum.

In summary, the embodiment of the interrogation system 100 described herein has a photon generator 110 and a plurality of detectors 112 located in the proximity of the container 106. The photon generator 110 generates photons that are directed into the container 106. The photons induce photonuclear reactions, which causes elements within the container 106, and possibly the container 106 itself, to emit neutrons. The photo-induced neutrons are detected by the detectors 112 and analyzed by electronics and other devices, such as computers, associated with the detectors 112. The photo-induced neutrons are classified as either prompt or delayed. Prompt neutron emission results from the direct photon interaction with the nucleus of an element. Delayed neutrons occur from photofission-induced and neutron fission-induced, fission fragments. The emission of delayed neutrons from the container 106 is a positive indication that the container 106 contains a nuclear material.

The detectors 112 enable the interrogation system 100 to discriminate between delayed neutrons and prompt neutrons. As set forth above, the detection of delayed neutrons indicates that the container 106 contains nuclear material. Prompt neutrons will help characterize any shield materials associated with the nuclear material. For example, if combined with conventional x-ray radiography, an anomalously high photoneutron signal from areas surrounding a very dense object may indicate significant low-density, neutron shielding materials.

Having summarily described the interrogation system 100, it will now be described in greater detail. In the non-limiting embodiment described herein, the photon generator 110 has an electron accelerator 116, a converter 117, and a collimator 118 among other components. The electron accelerator 116 may, as a non-limiting example, be an electron accelerator having selectable beam energies up to 12 MeV. The converter 117 may, as a non-limiting example, is a high atomic number converter. It should be noted that the photon generator 110 described herein is an example of a photon source and that other photon sources may be used in conjunction with the interrogation system 100.

In one embodiment, the accelerator 116 generates a beam of electrons and pulses up to a rate of several hundred hertz. The electrons are converted to high energy photons by way of the high atomic number converter 117, wherein the high energy photons have energies up to the maximum electron beam energy. The photons are sometimes referred to as bremsstrahlung photons. The photons generated at the converter 117 are collimated to a preselected annular width by the collimator 118. The process of generating a voluminous number of photons using a single pulse of electrons generated from a pulsed, electron accelerator is sometimes referred to as a photon flash event.

The high-energy photons generated by the photon generator 110 are forward-directed toward the container 106. The-above-described high-energy photons have the ability to pass through many different shielding configurations. For example, the energy of the electron accelerator 116 may be selected in order to provide photons with energy spectra appropriate for optimal penetration of a given shield. Thus, the photons are able to pass through the walls of the container 106 as well as most shielding that may be used to conceal or smuggle nuclear materials in a given container. The photons react with the container 106 itself and materials within the container to induce photonuclear reactions with the container 106 and its contents causing neutrons to be emitted from the container 106.

Neutrons from a photoneutron reaction (γ,n) are emitted promptly after the reaction occurs. Thus, the photoneutrons are referred to as prompt photoneutrons. Photofission reactions (γ,fission) emit both prompt and delayed neutrons. The delayed neutrons occur from the decay of the unstable fission products. For a selected electron beam energy operation, the detected neutrons, measured between accelerator pulses, have a time-dependent response that allows the identification of delayed neutrons. These delayed neutrons, resulting from the fission process, are separable in time from the prompt neutron signature. As described above, the emission of delayed neutrons is a positive indication that the container 106 contains nuclear material. Furthermore, to identify or discriminate between nuclear material types, i.e., depleted uranium, HEU, and thorium, a ratio of delayed neutron counts at two different electron beam energies may be utilized. The use of two different electron energy beams is referred to as the dual-beam energy technique. In one embodiment, the dual-beam energy technique enables the interrogation system 100 to differentiate between the three common types of nuclear materials. Thus, most threats associated with the nuclear materials may be readily evaluated.

Figure 2A:
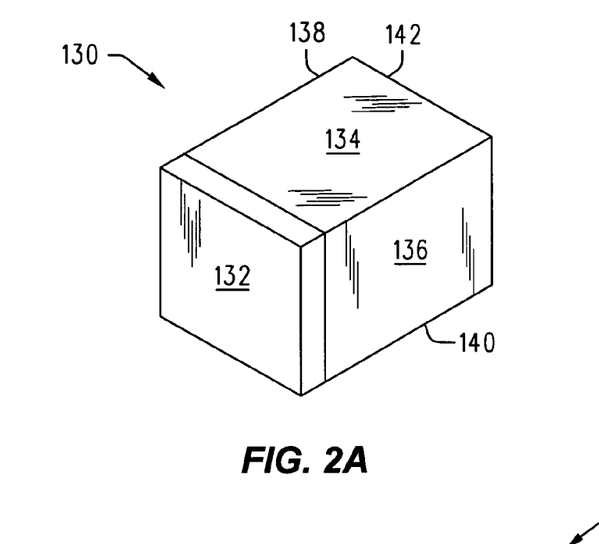
FIG. 2A is a rear perspective view of a detector.

The detectors 112 detect neutrons emitted from the container 106. As described in greater detail below, the detectors 112 and their associated electronics are able to distinguish between prompt and delayed neutrons in the presence of background x-rays, i.e., photons, caused by the electron accelerator 116, the collimator 118, and other structural materials associated with the interrogation system 100. A non-limiting example of a detector 130 is shown in FIG. 2A. The detector 130 of FIG. 2A is an example of one of the detectors 112 of FIG. 1. The detector 130 illustrated herein is substantially parallel-piped, however, it should be noted that the detector 130 may be virtually any shape. For example, the detector 130 may be substantially cylindrical. The detector 130 described herein has a rear panel 132, a top side, 134, a right side 136, a left side 138, a bottom side 140, and a front side 142. As described in greater detail below, the rear panel 132 is removable and the front side 142 is adapted to face the container 106, FIG. 1.

Figure 2B:
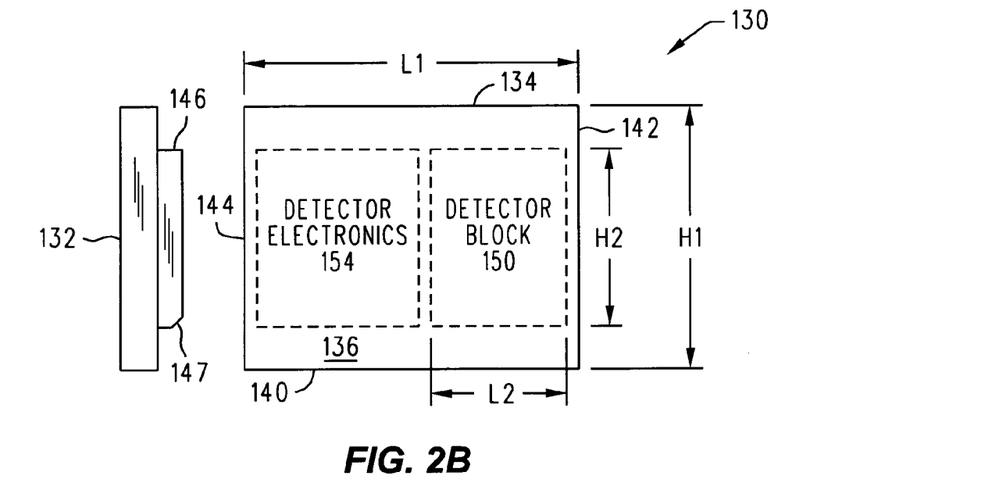
FIG. 2B is a side view of the detector of FIG. 2A.

A side view of the detector assembly 130 with the rear panel 132 removed therefrom is shown in FIG. 2B. The detector assembly 130 has a length L1 extending between a rear side 144 to which the rear panel 132 fits and the front side 142. The length L1 may, as an example, be approximately 35.56 centimeters. The detector assembly 130 may have a height H1 extending between the top side 134 and the bottom side 140. The height H1 may, as an example, be approximately 25.4 centimeters. As described above, the rear panel 132 shown in FIG. 2B is removed from the remaining portion of the detector 130. As shown in FIG. 2B, the rear panel 132 has a sealing portion 146 that fits into an interior portion of the detector 130. The use of the rear panel 132 serves to prevent neutrons and electromagnetic interference from entering the interior of the detector 130. More specifically, the detector 130, based on the neutron absorptive materials selected (borated polyethylene), is more sensitive to neutrons entering the front side 142 than other areas. Thus, the majority of neutrons entering the detector 130 will have been emitted from the container 106. The sealing portion 146 has a notch 147 formed therein that serves to pass wires between the interior and the exterior of the detector 130.

The interior of the detector assembly 130 is adapted to receive a detector block 150. In one embodiment of the detector assembly 130, the detector block 150 is inserted into and removed from the detector assembly 130 by way of the rear side 144 of the detector assembly 130. As described in greater detail below, the detector block 150 has neutron detectors located therein and serves, in conjunction with the detector electronics 154, to detect neutrons emitted by material within the container 106, FIG. 1. In addition to the detector block 150, detector electronics 154 may be received within the interior of the detector 130 via the rear side 144.

Figure 2C:
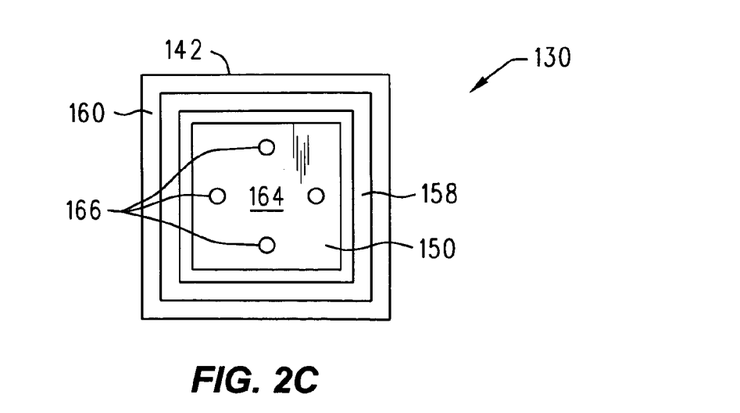
FIG. 2C is an end view of the detector of FIG. 2A.

A front view of the detector assembly 130 is shown in FIG. 2C. The detector block 150 is formed from a virgin polyethylene block or a plurality of blocks. The detector block 150 has front surface 164 that has a plurality of holes 166 formed therein. The holes 166 described herein have diameters of approximately 2.64 centimeters and lengths of approximately eight centimeters. Each of the holes 166 are adapted to receive a neutron detector and a polyethylene plug having a diameter of approximately 1.27 centimeters. The polyethylene plug may be located between the neutron detector, not shown in FIG. 2C, and the front surface 164 of the polyethylene block 150. In one embodiment, each polyethylene plug is flush with the front surface 164 of the detector block 150. One example of a neutron detector that may be located in one of the holes 166 is a 10-atmosphere helium-3 neutron detector. With additional reference to FIG. 2B, the neutron detectors are operatively or otherwise electrically connected to the detector electronics 154, FIG. 2B. The embodiment of the detector 130 described herein has four holes 166 to receive four neutron detectors. It should be noted that the detector assembly 130 may be adapted to have any number of neutron detectors located therein.

The detector assembly 130 includes several layers of materials that serve to attenuate electromagnetic interferences in the detector electronics 154, FIG. 2B and to attenuate "room return" neutron noise signals. The detector 130 has an inner layer 158 and an outer layer 160. The inner layer 158 is, as a non-limiting example, borated polyethylene and is approximately 5.08 centimeters thick. The polyethylene is borated at approximately five percent by weight. The neutron die-away time for this configuration is approximately sixty-eight seconds, wherein the die-away time is the time required for the neutron population within the detector block 150 to decrease by one exponential value. The outer layer 160 is approximately 0.05 centimeters thick and comprises cadmium. The outer layer 160 of cadmium serves to remove any external thermal neutrons below a defined energy value. In one embodiment of the detector assembly 130, an electromagnetic shield surrounds the outer layer 160. The shield may, as non-limiting examples, be a layer of copper or aluminum that is approximately 0.1 centimeters thick.

Having described the detector block 150, the detector electronics 154 will now be described. A block diagram of the detector electronics 154 is described followed by an embodiment of a more detailed circuit diagram.

Figure 3:
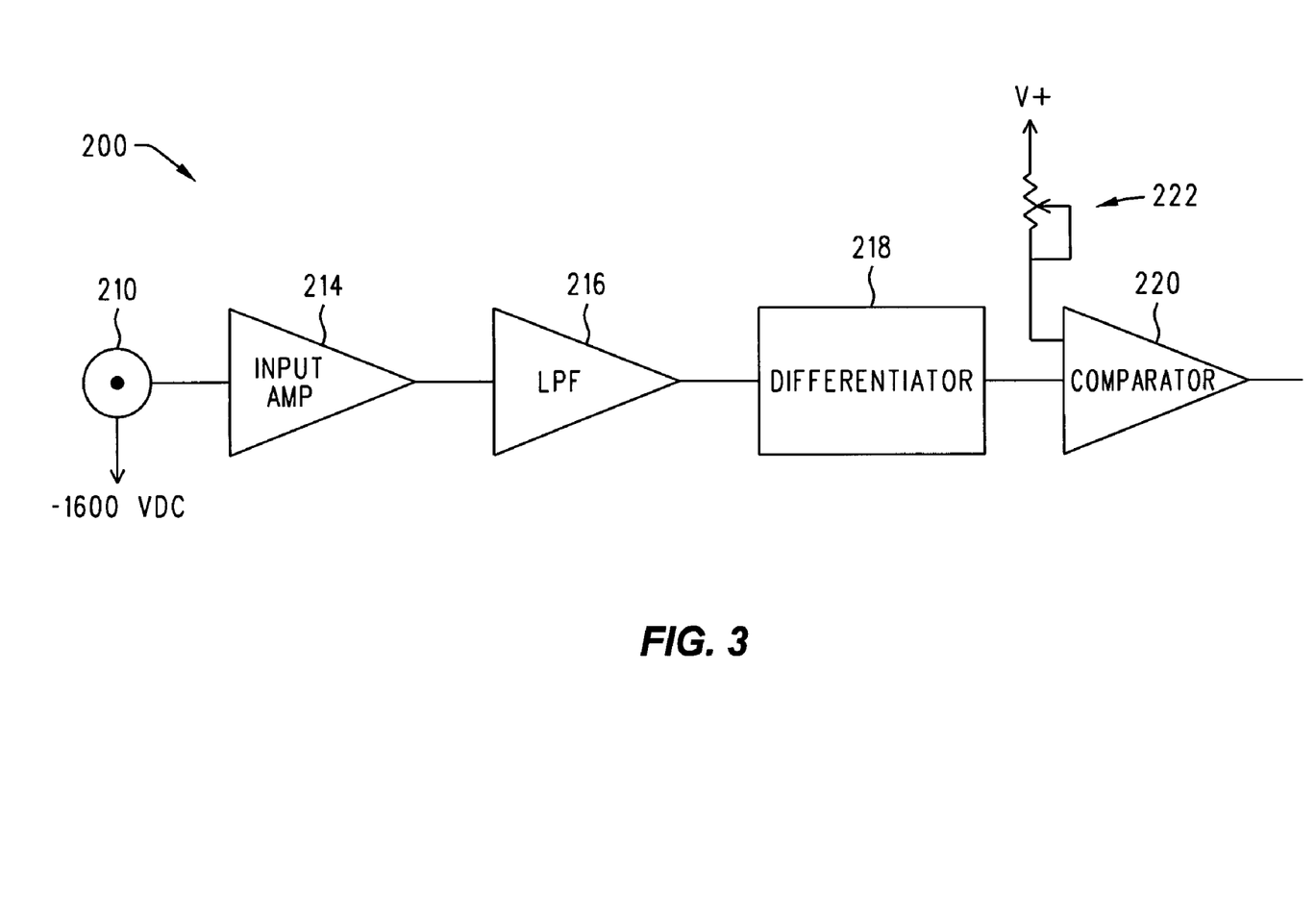
FIG. 3 is a schematic diagram of an embodiment of a preamplifier of the nuclear detection system of FIG. 1.
Figure 4:
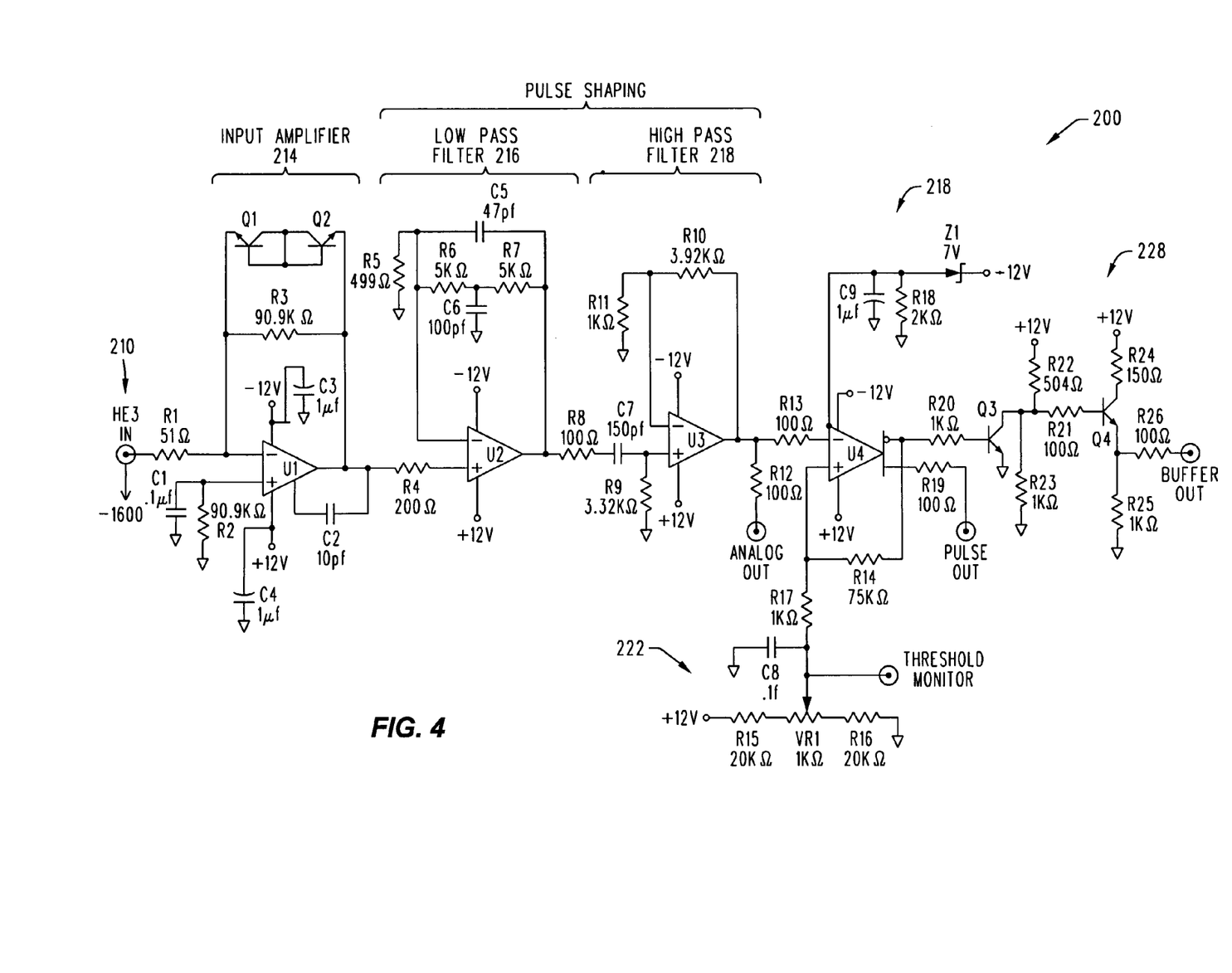
FIG. 4 is a detailed schematic diagram of an embodiment of the preamplifier of FIG. 3.

Referring additionally to FIG. 3, each of the neutron detectors described above has a preamplifier 200 operatively or otherwise electrically connected thereto. Accordingly, the detector electronics 154 of FIG. 2B has four preamplifiers 200 associated therewith; one for each of the helium-3 detectors. The non-limiting embodiment of the preamplifier 200 described herein is connected to a neutron detector 210 and has an input amplifier 214, a low-pass filter (LPF) 216, a high-pass filter (HPF) 218, sometimes referred to as a differentiator, a comparator 220, and a voltage adjustment 222. The following description focuses on a single neutron detector 210 associated with a preamplifier 200 as shown in FIGS. 3 and 4. It should be noted that the detectors 112, FIG. 1, may have any number of neutron detectors associated therewith.

In the embodiment of the preamplifier 200 described herein, the neutron detector 210 has two conductors; a case and a center conductor. The case of the neutron detector 210 is biased at approximately negative sixteen hundred to negative eighteen hundred volts relative to the center conductor, which operates at a nominal voltage of zero volts. This biasing arrangement allows the neutron detector 210 to be direct-coupled to the input amplifier 214. The direct-coupling between the neutron detector 210 and the input amplifier 214 reduces the signal processing time between the neutron detector 210 and the subsequent processing by the other components of the preamplifier 200. The preamplifier 200 enables the relatively weak signals generated by the neutron detector 210 to be processed.

As described in greater detail below, the input amplifier 214 is a current-sensing amplifier. Current generated by the neutron detector 210, upon detection of neutrons, is detected and amplified by the input amplifier 214. The low-pass filter 216 serves as a pulse-shaping, low-pass filter. The low-pass filter 216 has a very short pulse rise time. For example, the pulse rise time may be approximately 0.5 microseconds. This short pulse rise time serves to reduce the probability of a detection pulse being detected and processed during the processing of an earlier detected pulse.

The high-pass filter 218 serves to further shape the above-described pulse. This shaping of the pulse improves the ability of the preamplifier 200 to process individual neutron pulses even though the neutron detector 210 may have not completely recovered from a photon flash event. Because of the low-pass filter 216 being coupled to the high-pass filter 218, the neutron detector assembly 130, FIG. 2A, is capable of operating with minimal shielding in high radiation fields.

The comparator 220 described herein is a high-speed differential comparator. The comparator 220 compares the pulse generated by the high-pass filter 218 to a threshold voltage that is established by the voltage adjustment 222. When the input voltage from the high-pass filter 218 exceeds a threshold voltage established by the voltage adjustment 222, the comparator 220 outputs a pulse. The pulse may be transistor-to-transistor logic (TTL) compatible so as to be registered by a conventional counter. The use of the comparator 220 reduces the probability that pulses generated by noise will be processed as detected neutrons. More specifically, only pulses that have a voltage high enough to be processed as detected neutrons are able to exceed the threshold voltage established by the voltage adjustment 222. Pulses resulting from noise generally do not have voltages that are high enough to exceed the threshold established by the voltage adjustment 222.

Having generally described an embodiment of the preamplfier 200, it will now be described in greater detail.

A detailed schematic diagram of a non-limiting embodiment of the preamplifier of FIG. 3 is shown in FIG. 4. The component values shown in FIG. 4 and described herein are for illustration purposes only. One skilled in the art may change the values while achieving similar results within the scope of this description.

The input amplifier 214 consists of an operational amplifier U1 and its associated components. In one embodiment of the preamplifier 200, the operational amplifier U1 is an LM7171 amplifier that is commercially available from the National Semiconductor Corporation. The inverting input of the operational amplifier U1 is connected to the center conductor of the neutron detector 210 by way of a resistor R1. The non-inverting input of the operational amplifier U1 is connected to ground by way of a parallel combination of a capacitor C1 and a resistor R2. The combination of the capacitor C1 and the resistor R2 serves as an input bias for the non-inverting input of the operational amplifier U1 as well as noise reduction. Frequency compensation is provided by a capacitor C2.

The feedback of the operational amplifier U1 consists of a resistor R3 connected in parallel to the combination of a transistor Q1 and a transistor Q2. The resistor R3 provides a high gain for the input amplifier 214. The transistor Q1 and the transistor Q2 are wired as back-to-back diodes in order to prevent output saturation of the operational amplifier U1. The operational amplifier U1 is powered by positive and negative twelve volt power supplies, which are used throughout the preamplifier 200. The voltage inputs to the operational amplifier U1 are connected to ground by a capacitor C3 and a capacitor C4 in order to attenuate noise on the power lines.

The output of the input amplifier 214 is direct coupled to the input of the low-pass filter 216. The low-pass filter 216 consists of a operational amplifier U2 and its associated components. In one embodiment, the operational amplifier U2 is an LM7171 and is commercially available from the National Semiconductor Corporation. The output of the operational amplifier U1 is connected to the non-inverting input of the operational amplifier U2 via a resistor R4. The feedback components of the capacitor C5, the capacitor C6, the resistor R5, the resistor R6, and the resistor R7 provide low-pass filtering. The configuration of the low-pass filter 216 provides for a pulse rise time of approximately 0.5 microseconds. The response of the low-pass filter 216 described herein provides for approximately 3.0 dB attenuation at approximately 338 kilohertz.

The output of the low-pass filter 216 is connected to the high-pass filter 218. More specifically, the output of the operational amplifier U2 is connected to the non-inverting input of an operational amplifier U3 by way of a resistor R8 and a capacitor C7. In one embodiment, the operational amplifier U3 is an LM7171 operational amplifier and is commercially available from the National Semiconductor Corporation. The feedback associated with the operational amplifier U3 consists of a resistor R10 and a resistor R11, which provides for a gain of approximately five. The differentiation or high-pass filtering is achieved by way of the resistor R8, the resistor R9, and the capacitor C7. The response of the high-pass filter 218 described herein provides approximately 3.0 dB at approximately 319 kilohertz.

The output of the operational amplifier U3 and, thus the high-pass filter 218, is an analog representation of neutrons detected by the neutron detector 210. This analog output may be measured at the terminal referenced ANALOG OUT, which is connected to the output of the operational amplifier U3 via a resistor R12. Voltage pulses on the ANALOG OUT terminal represent the detection of neutrons.

The output of the operational amplifier U3 may have some photon-related noise. In order to distinguish between noise and detected neutrons, the output of the differentiator 218 is connected to the comparator 220. The comparator 220 includes an operational amplifier U4 and its associated components. In one embodiment, the operational amplifier U4 is an industry standard LM361 high-speed differential comparator. The inverting input of the operational amplifier U4 is connected to the output of the operational amplifier U3 by way of a resistor R13.

Voltage comparison is achieved by creating a desired voltage at the voltage adjustment 222 and applying this voltage to the non-inverting input of the operational amplifier U4. A feedback resistor R14 is also used in conjunction with the voltage comparison. The voltage adjustment 222 consists of a variable resistor VR1, a resistor R15, a resistor R16, a resistor R17, and a capacitor C8. The voltage applied to the non-inverting input of the operational amplifier U4 is determined by adjusting the variable resistor VR1. High and low limits of the voltage are established by the resistor R15 and the resistor R16. Noise and ripple are attenuated by the capacitor C8 and buffering is provided by the resistor R17. The voltage established by the voltage adjustment 222 may be monitored at the terminal designated THRESHOLD MONITOR.

The output voltage of the operational amplifier U4 is limited by the voltage at the VCC. In order to provide a TTL output, the VCC is set at five volts. In order to limit the number of power supplies required to operate the preamplifier 200, the five volt VCC may be established by dropping seven volts across a zener diode Z1, which is connected between the twelve volt power supply and VCC. A capacitor C9 is connected between VCC and ground to attenuate noise and ripple on the VCC. Resistor R18 provides bias current for Z1. The operational amplifier U4 has an inverting and non-inverting output. In the non-limiting embodiment described herein, the non-inverting output is monitored via a resistor R19 at a terminal referenced as PULSE OUT.

The embodiment of the preamplifier 200 described in FIG. 4 has a buffer 228 operatively or otherwise electrically connected to the comparator 220. The buffer 228 comprises two NPN transistors, Q3 and Q4, and their associated biasing components. The transistors Q3 and Q4 described herein are industry standard 2N3904 devices. The base of the transistor Q3 is connected to the inverting output of the operational amplifier by way of a resistor R20. The emitter of the transistor Q3 is connected to ground and the collector is biased by resistors R22 and R23. Accordingly, the transistor Q3 functions as an inverter. The collector of the transistor Q3 is connected to the base of the transistor Q4 by way of a resistor R21. The transistor Q4 functions as a non-inverting switch and is biased by the resistors R24 and R25. The buffered output of the preamplifier 200 is at the emitter of the transistor Q4. A resistor R26 is located between the emitter and an output referenced as BUFFER OUT, which serves to reduce oscillations.

It should be noted that other configurations may be used to create a buffer. For example, the buffer 228 may comprise a line driver or buffer consisting of an LM6221 line driver available from the National Semiconductor Corporation.

The preamplifier 200 is able to detect neutrons emitted from the container 106, FIG. 1, within microseconds of an accelerator-produced, photon flash event. This rapid detection of neutrons enables the preamplifier 200 to be able to distinguish between prompt and delayed neutrons in the presence of background noise created from the production of photon flash events. The rapid detection also enables the container 106, FIG. 1, to undergo repeated photonuclear stimulation. For example, the generator 110 may stimulate the container 106 with repetition rates up to several hundred hertz thereby increasing the accuracy of the detection and reducing the time required for detection. Therefore, the container 106, FIG. 1, is able to undergo rapid photonuclear stimulation and the preamplifier 200 is able to accurately and rapidly detect the emission of both prompt and delayed neutrons. As described above, the detection of delayed nuetrons is a positive indiction that nuclear materials are present within the container 106.

Having described the components of the interrogation system 100, the operation of the interrogation system 100, including the preamplifier 200 will now be described.

Referring to FIG. 1, the interrogation system 100 is located in close proximity to the container 106. In one embodiment, the photon generator 110 and the detectors 112 are placed approximately one meter from the container 106. In some embodiments, this placement of the detectors 112 is approximately two meters from the center of the container 106. High energy photons are emitted from the photon generator 110 to induce photonuclear reactions with the contents of the container 106. The photonuclear reactions cause neutrons to be emitted from the container 106, which are detected by the detectors 112. As described above, many materials will emit prompt neutrons, however, only nuclear materials emit delayed neutrons.

Referring to FIG. 4, the neutron detector 210 generates a voltage pulse upon detecting a neutron. It should be noted that the preamplifier 200 is able to detect neutrons during the detector's flash recovery period which may last up to several hundred microseconds after each accelerator pulse. Therefore, the detectors 112, FIG. 1, are able to detect both prompt and delayed neutrons. The pulse is amplified by the input amplifier 214. The configuration of the transistor Q1 and the transistor Q2 in the feedback of the operational amplifier U1 serves to prevent the operational amplifier U1 from saturating and further serves to lock out the remaining pre-amplifier circuitry. Without saturating the operational amplifier U1, the input amplifier 214 is able to discriminate between rapidly detected neutrons. The input amplifier 214 outputs pulses that are representative of detected neutrons. The signal generated by the input amplifier 214, however, may have some significant noise due to the photon flash response.

The signal generated by the low-pass filter 216 consists of a plurality of pulses, wherein each pulse is representative of a detection by the neutron detector 210. The pulses are shaped by the low-pass filter 216 and the high-pass filter 218 to be well defined pulses. These pulses may be monitored at the terminal ANALOG OUT. In order to further distinguish pulses detected by the neutron detector 210 and neutron signal noise, the output of the high-pass filter 218 is input to the voltage comparator 220. The signal is compared to a pre-selected voltage set via voltage adjustment 222. The signal that is representative of the detected pulses is typically greater than the noise floor. Therefore, by setting the voltage of the voltage adjustment 222 slightly greater than the noise floor, the comparator 220 will only pass pulses and the noise will be significantly attenuated. The pulses generated by the comparator 220 may be monitored at the PULSE OUT terminal. In order to make the output of the preamplifier 200 TTL compatible, the buffer 228 converts the pulses generated by the comparator 220 to five-volt pulses and enables the preamplifier 200 to be coupled with other instruments.

The pulses generated by the preamplifier 200 may be monitored by a conventional monitoring device, such as a counter or an oscilloscope. Thus, a determination as to whether the container 106, FIG. 1, produced delayed neutrons may be readily determined. In addition, the interrogating photons can be used to provide an x-ray radiograph of the container contents and help located very dense materials representative of nuclear materials. Specifically, the axially-dependent neutron emission signals can be correlated with the container radiograph to help verify nuclear material detection. This correlation may be performed during the axial development of a radiograph, e.g., real time inspection, or when the interrogation system 100 is repositioned, e.g., manual inspection, at the suspicious object location.

Figure 5:
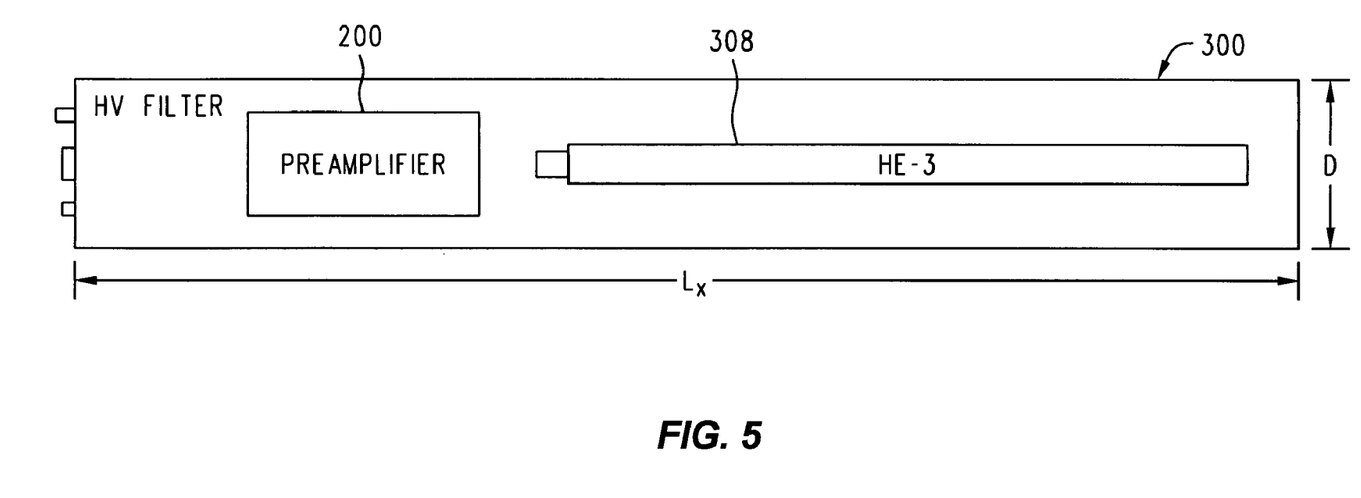
FIG. 5 is a cutaway schematic view of an embodiment of a detector.

Another embodiment of the interrogation system 100 uses a modified detector assembly 300, FIG. 5, to increase counting efficiencies. The detector 300 of FIG. 5 also uses the preamplifier 200 described above. The detector 300 may be cylindrical and may have a length X of approximately 44.5 inches and a diameter D of approximately 3.9 inches. The detector 300 may weigh, as a non-limiting example, tube 308. In the non-limiting embodiment described herein, the tube 308 is a 10.0 atmosphere, helium-3 tube that is approximately 30.0 inches long. It should be noted that the tube 308 is electrically or otherwise operatively connected to the preamplifier 200.

Figure 6A:
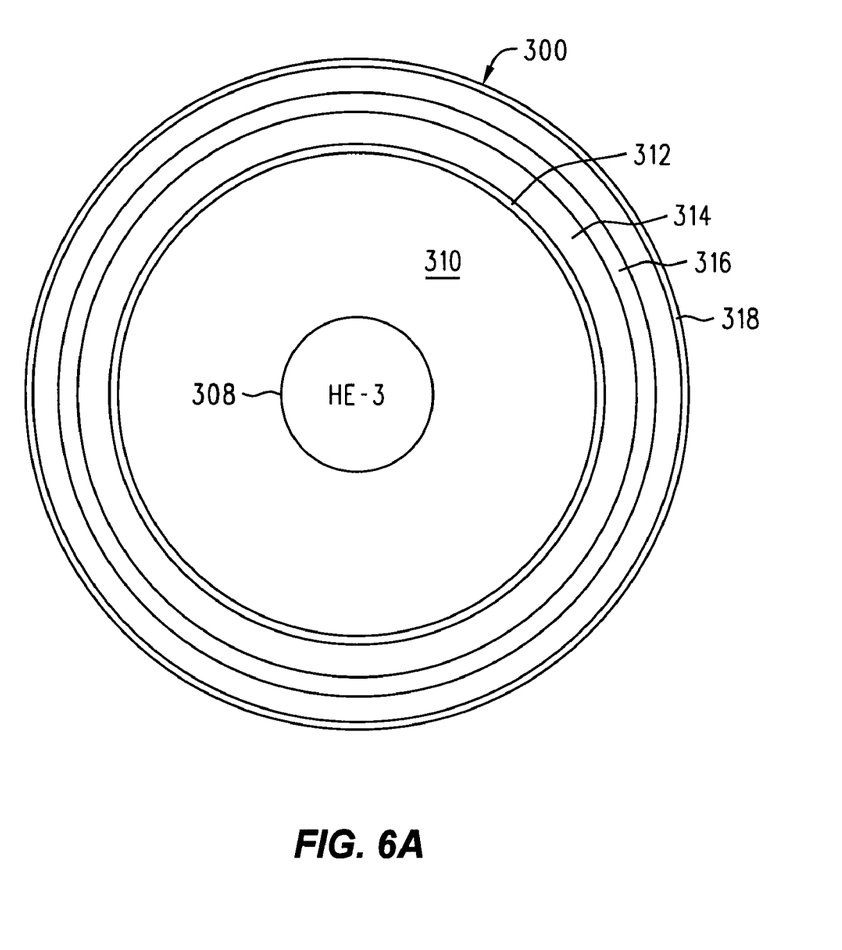
FIG. 6A is an side, cross-sectional view of an embodiment of the detector of FIG. 5.

A side, cross-sectional view of an embodiment of the detector 300 is shown in FIG. 6A. As shown in FIG. 6A, the tube 308 is surrounded by a plurality of concentric rings of differing materials that serve to suppress "room-return"-type thermal neutrons, which are considered to be noise. A first ring 310 consists of a one-inch thick polyethylene sleeve to effectively moderate the energetic neutrons emitted from the container 106, FIG. 1. A second sleeve 312 is located adjacent the first sleeve 310 and consists of cadmium. In one embodiment, the second sleeve is approximately 0.045 inches thick. A third sleeve 314, a fourth sleeve 316, and a fifth sleeve 318 consists of multiple borated polyethylene segments enriched with 26% boron-10. The third sleeve 314, the fourth sleeve 316, and the fifth sleeve 318 each may be approximately 0.125 inches thick.

Caps, not shown, may be located at the ends of the detector 300. In an axial manner, the caps may match the radial shielding composition described with reference to FIG. 6A. The detector 300 may be covered by a 0.094 inch thick aluminum housing to provide structural protection and electromagnetic shielding.

Figure 6B:
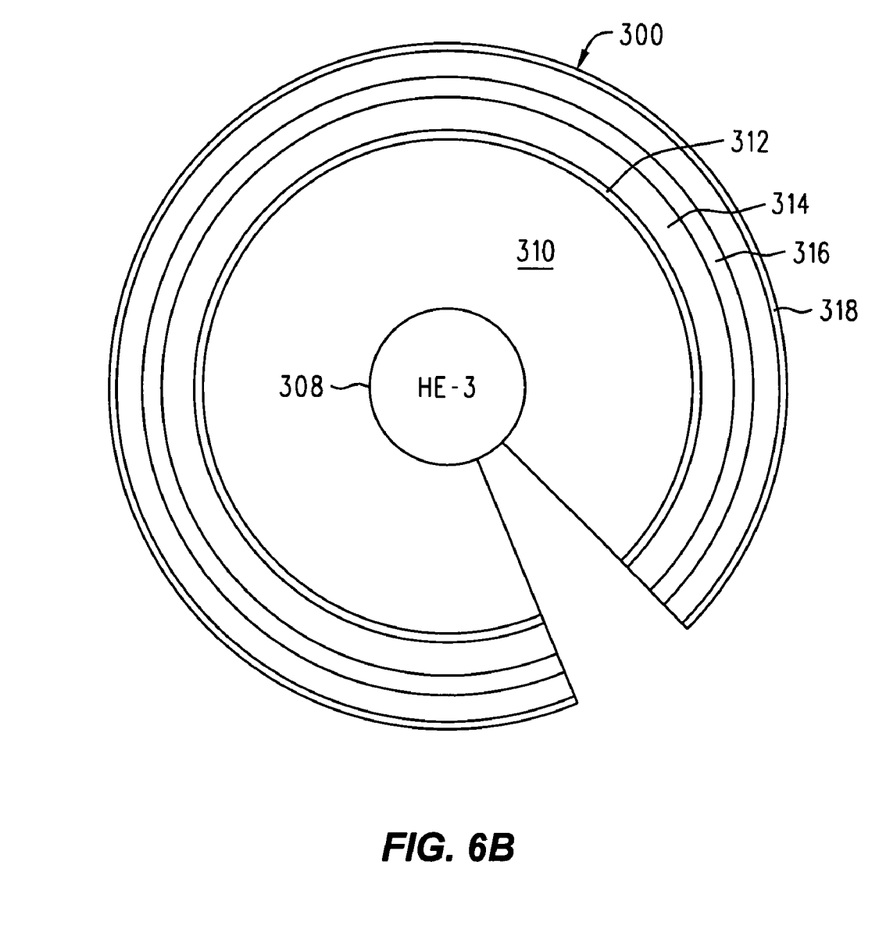
FIG. 6B is an side, cross-sectional view of an embodiment of the detector of FIG. 5 wherein the detector is at least partially surrounded by at least one material.

An embodiment of the detector 300 is shown in FIG. 6B wherein the above-described materials at least partially surround the tube 308.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. A device for detecting photonuclear-induced neutrons, said device comprising:
   a neutron detector comprising a detector output; and
   a detection circuit connected to said detector output, said detection circuit comprising:
      an amplifier comprising an amplifier input and an amplifier output, said amplifier input being connected to said detector output;
      a low-pass filter comprising a low-pass filter input and a low-pass filter output, said low-pass filter input being connected to said amplifier output; and
      a high-pass filter comprising a high-pass filter input and a high-pass filter output, said high-pass filter input being connected to said low-pass filter output.

2. The device of claim 1, and further comprising a comparator, said comparator comprising a signal input, a threshold input, and a comparator output; said signal input being operatively connected to said high-pass filter output;

said comparator output being in a first operative state when a voltage at said signal input is less than a voltage at said threshold input, and said comparator output being in a second operative state when a voltage at said signal input is greater than a voltage at said threshold input.

3. The device of claim 1, and further comprising an analyzer operatively connected to said detection circuit, wherein pulses generated by said detection circuit are detectable by said analyzer.

4. The device of claim 1, and further comprising a buffer operatively connected to said detection circuit.

5. The device of claim 4, wherein said buffer provides a transistor to transistor logic output.

6. The device of claim 1, wherein said neutron detector and said detection circuit have a photon flash recovery response associated therewith, and wherein said photon flash recovery response is small enough to distinguish between prompt and delayed neutrons.

7. The device of claim 1, wherein said detector further comprises a housing and a voltage supply located within said housing.

8. The device of claim 1, wherein said detector further comprises an He-3 tube.

9. The device of claim 1 and further comprising a photon generator.

10. The device of claim 9, wherein said photon generator comprises an electron accelerator.

11. The device of claim 1, and further comprising neutron shielding wherein photoneutron signal noise is suppressable by said neutron shielding.

12. The device of claim 1, wherein said detector comprises a tube surrounded by a plurality of materials.

13. The device of claim 12, wherein said tube comprises helium.

14. The device of claim 12, wherein one of said a plurality of materials comprises polyethylene.

15. The device of claim 12, wherein one of said a plurality of materials comprises cadmium.

16. The device of claim 12, wherein one of said a plurality of materials comprises borated-polyethylene material.

17. The device of claim 12, wherein one of said a plurality of materials comprises aluminum.

18. The device of claim 1, wherein said detector comprises a helium tube surrounded by a first layer comprising polyethylene, said first layer surrounded by a second layer comprising cadmium; said second layer surrounded by a third layer comprising borated polyethylene.

* * * * *